(12) United States Patent
Hirai et al.

(10) Patent No.: US 9,096,523 B2
(45) Date of Patent: Aug. 4, 2015

(54) PROCESS FOR PREPARING CYCLIC AMINE COMPOUNDS

(75) Inventors: Yoshinori Hirai, Takasago (JP); Akira Nishiyama, Takasago (JP)

(73) Assignee: KANEKA CORPORATION, Osaka (JP)

(*) Notice: Subject to any disclaimer, the term of this patent is extended or adjusted under 35 U.S.C. 154(b) by 0 days.

(21) Appl. No.: 13/980,162

(22) PCT Filed: Mar. 28, 2012

(86) PCT No.: PCT/JP2012/058061
§ 371 (c)(1),
(2), (4) Date: Jul. 17, 2013

(87) PCT Pub. No.: WO2012/133486
PCT Pub. Date: Oct. 4, 2012

(65) Prior Publication Data
US 2013/0303771 A1    Nov. 14, 2013

(30) Foreign Application Priority Data

Mar. 31, 2011 (JP) ................................. 2011-079033

(51) Int. Cl.
*A01N 43/40* (2006.01)
*C07D 211/60* (2006.01)
(52) U.S. Cl.
CPC .................................... *C07D 211/60* (2013.01)
(58) Field of Classification Search
CPC .................................................... A61K 31/445
USPC ........................................................ 514/315
See application file for complete search history.

(56) References Cited

U.S. PATENT DOCUMENTS

| 5,200,561 | A | 4/1993 | Konya et al. |
| 8,288,553 | B2 | 10/2012 | Priour et al. |
| 2010/0197928 | A1* | 8/2010 | Priour et al. ................... 546/244 |
| 2012/0323010 | A1 | 12/2012 | Ronsheim et al. |
| 2013/0012712 | A1 | 1/2013 | Priour et al. |
| 2014/0163230 | A1 | 6/2014 | Ronsheim et al. |

FOREIGN PATENT DOCUMENTS

| JP | 05-009158 A | 1/1993 |
| JP | 2009-073739 A | 4/2009 |
| WO | 2008/125578 A2 | 10/2008 |
| WO | 2009/090320 A1 | 7/2009 |
| WO | 2012/172368 A1 | 12/2012 |
| WO | WO 2012/172368 | * 12/2012 |

OTHER PUBLICATIONS

Rohm and Haas "Enhancing Borohydride's Reductive Selectivity", Oct. 2003.*
Cheng, M. et al., "Design, Synthesis, and Biological Evaluation of Matrix Metalloproteinase Inhibitors Derived from a Modified Proline Scaffold", Journal of Medical Chemistry, American Chemical Society, US, vol. 42, No. 26, Jan. 1, 1999, pp. 5426-5436, Cited in Extended European Search Report dated Jul. 15, 2014.
Extended European Search Report dated Jul. 15, 2014, issued in corresponding European Patent Application No. 12762930.1 (8 pages).
International Search Report dated May 29, 2012, issued in corresponding application No. PCT/JP2012/058061.

* cited by examiner

*Primary Examiner* — John Mabry
(74) *Attorney, Agent, or Firm* — Westerman, Hattori, Daniels & Adrian, LLP

(57) ABSTRACT

A cyclic amine compound having a prescribed configuration can be efficiently prepared by reducing an imine derivative in the presence of a sulfonic acid. Specifically, a cyclic amine compound which is substituted with an amino group and a carboxyl group in which both groups are arranged in the trans configuration can be prepared efficiently.

10 Claims, No Drawings

PROCESS FOR PREPARING CYCLIC AMINE COMPOUNDS

TECHNICAL FIELD

The present invention relates to a process for producing a cyclic amine compound, specifically, a cyclic amine compound which has an amino group and a carboxyl group as substituents and their configuration is trans, and especially a trans-5-aminopiperidine-2-carboxylic acid derivative, which is useful for an intermediate for pharmaceuticals.

BACKGROUND ART

The process represented in the following scheme is known for producing a trans-5-aminopiperidine-2-carboxylic acid derivative, which is useful for an intermediate for pharmaceuticals.

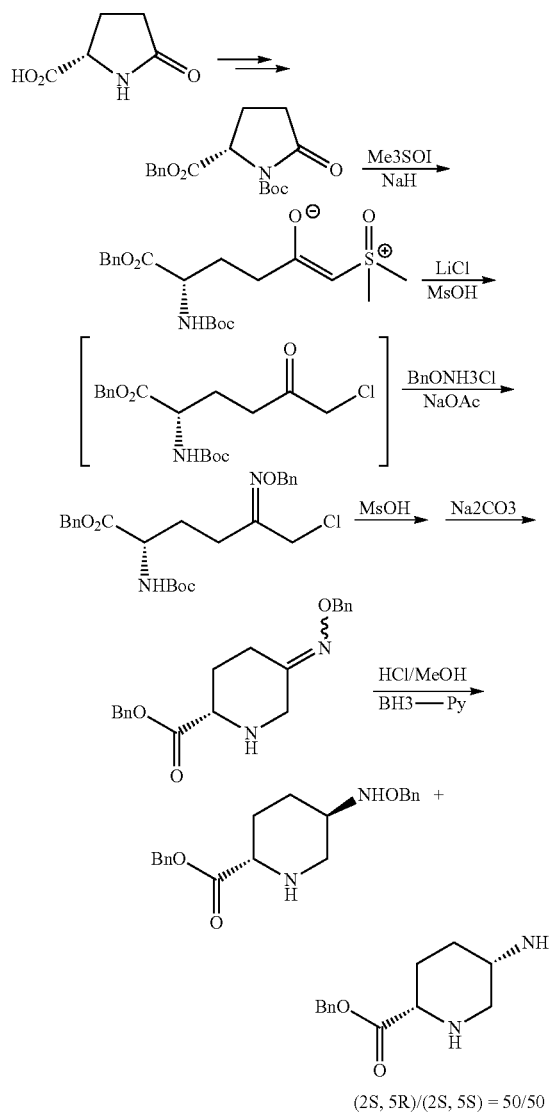

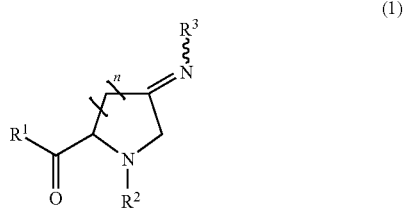

(2S, 5R)/(2S, 5S) = 50/50

In this method, L-pyroglutamic acid is protected by introducing a benzyl group at the carboxylic acid and introducing a tert-butoxycarbonyl group (a Boc group) at the amino group, and then coupling reaction with a sulfoxonium ylide is carried out. Next, the obtained compound is converted into a chloroketone, and is subsequently reacted with benzyloxyamine to obtain a corresponding imine derivative. Following deprotection of the above Boc group and the cyclization under basic condition lead to (S)-5-(benzyloxyimino)-piperidine-2-carboxylic acid benzyl ester. The reaction with borane-pyridine-complex in the presence of a hydrogen chloride leads to (2S)-5-(benzyloxyamino)-piperidine-2-carboxylic acid benzyl ester, then a salt is formed between oxalic acid, and the isolation is performed (Patent Document 1).

PRIOR ART DOCUMENT

Patent Document

Patent Document 1: WO2009/090320

DISCLOSURE OF THE INVENTION

Problems to be Solved by the Invention

In the process described in the Patent Document 1, the target compound is obtained after forming a salt with oxalic acid as a diastereomer mixture, in which the (2S,5R) derivative (trans isomer) and the (2S,5S) derivative (cis isomer) exists in the ratio of 50:50. The diastereomer mixture can be separated with a purification method such as a chromatography, however, the unnecessary cis isomer is to be discarded, and therefore, the process has problems in points of producing efficiency, cost, and environmental load.

Means for Solving the Problems

Under the above-described circumstance, as a result of intensive study, the present inventors discovered that it is possible to produce a trans isomer of a cyclic amine compound efficiently by performing a reduction reaction of an imine derivative in the presence of a sulfonic acid, and accomplished the present invention.

The present invention relates to a process for producing a cyclic amine compound, comprising the step of reacting an imine derivative represented by the following formula (1):

(1)

wherein $R^1$ is an organic group forming an ester bond, an amide bond, or a thioester bond with the carbonyl group binding to $R^1$ itself; $R^2$ is hydrogen atom, $C_{1-12}$ alkyl group, $C_{2-12}$ alkenyl group, $C_{7-21}$ aralkyl group, or $C_{6-18}$ aryl group; $R^3$ is hydrogen atom, $C_{1-12}$ alkyl group, $C_{2-12}$ alkenyl group, $C_{7-21}$ aralkyl group, $C_{6-18}$ aryl group, hydroxy group, $C_{1-12}$ alkyloxy group, $C_{2-12}$ alkenyloxy group, $C_{7-21}$ aralkyloxy group, or $C_{6-18}$ aryloxy group; and n is an integer of 1, 2, or 3, with a reducing agent in the presence of a sulfonic acid, wherein the cyclic amine compound is represented by the following formula (2):

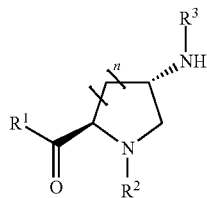

(2)

wherein $R^1$, $R^2$, $R^3$ and n are the same as the above or the reduced form thereof,
or the following formula (3):

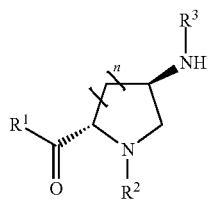

(3)

wherein $R^1$, $R^2$, $R^3$ and n are the same as the above or the reduced form thereof.

$R^1$ is, for example, $C_{1-12}$ alkyloxy group, $C_{2-12}$ alkenyloxy group, $C_{7-21}$ aralkyloxy group, $C_{6-18}$ aryloxy group, $C_{3-36}$ trialkylsilyloxy group, amino group, $C_{1-12}$ alkylamino group, $C_{2-12}$ alkenylamino group, $C_{7-21}$ aralkylamino group, $C_{6-18}$ arylamino group, $C_{2-24}$ dialkylamino group, $C_{4-34}$ dialkenylamino group, $C_{14-42}$ diaralkylamino group, $C_{12-36}$ diarylamino group, thiol group, $C_{1-12}$ alkylthio group, $C_{2-12}$ alkenylthio group, $C_{7-21}$ aralkylthio group, or $C_{6-18}$ arylthio group. The above sulfonic acid is preferably sulfuric acid, camphorsulfonic acid, or others; and the reducing agent is preferably borane.

The present invention includes, for example, a process for producing a trans isomer (50) of 5-(benzyloxyamino)-piperidine-2-carboxylic acid benzyl ester, wherein $R^1$ is benzyloxy group, $R^2$ is hydrogen atom, $R^3$ is benzyloxy group, and n is 2; and more preferably a process for producing (2S,5R)-5-(benzyloxyamino)-piperidine-2-carboxylic acid benzyl ester represented by the following formula (5):

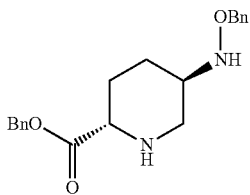

(5)

wherein $R^1$ is benzyloxy group, $R^2$ is hydrogen atom, $R^3$ is benzyloxy group, n is 2, and the carbon atom to which the group $R^1$CO is connected is in the S configuration.

The present invention also includes a process for producing a trans isomer (90) of 5-benzyloxyamino-piperidine-2-carboxylic acid dibenzylamide, wherein $R^1$ is dibenzylamino group, $R^2$ is hydrogen atom, $R^3$ is benzyloxy group, and n is 2; and more preferably a process for producing (2S,5R)-5-(benzyloxyamino)-piperidine-2-carboxylic acid dibenzylamide represented by the following formula (9):

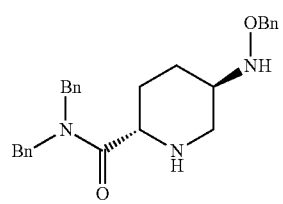

(9)

wherein $R^1$ is dibenzylamino group, $R^2$ is hydrogen atom, $R^3$ is benzyloxy group, n is 2, and the carbon atom to which the group $R^1$CO is connected is in the S configuration.

The present invention includes, for example, a process for producing a trans isomer (70) of a 5-(benzyloxyamino)-piperidine-2-carboxylic acid derivative in which $R^1$ is a group represented by the following formula (8):

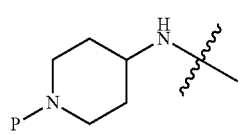

(8)

wherein P represents a protecting group for the amino group, preferably benzyloxycarbonyl group; $R^2$ is hydrogen atom; $R^3$ is benzyloxy group; and n is 2; and more preferably a process for producing a (2S,5R)-5-(benzyloxyamino)-piperidine-2-carboxylic acid derivative represented by the following formula (7):

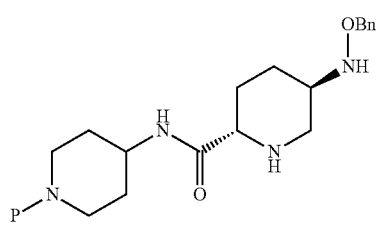

(7)

wherein $R^1$ is a group represented by the previous formula (8), $R^2$ is hydrogen atom, $R^3$ is benzyloxy group, n is 2, and the carbon atom to which the group $R^1$CO is connected is in the S configuration.

The obtained trans isomer (50) can form a salt with oxalic acid, to precipitate a solid in either one of the solvents selected from methanol, ethanol, isopropanol, a mixed solvent containing methanol, a mixed solvent containing ethanol, and a mixed solvent containing isopropanol.

Further, the present invention includes a process for producing a solid of (2S,5R)-5-(benzyloxyamino)-piperidine-2-carboxylic acid benzyl ester oxalate, wherein a salt is formed from (2S,5R)-5-(benzyloxyamino)-piperidine-2-carbocylic acid benzyl ester represented by the following formula (5):

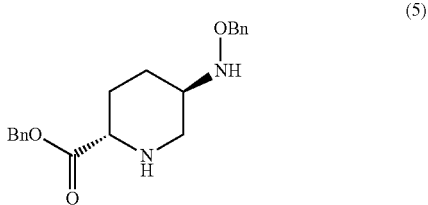 [SMILES: O=C(OCc1ccccc1)[C@@H]1CC[C@@H](NOCc2ccccc2)CN1]

containing (2S,5S)-5-(benzyloxyamino)-piperidine-2-carboxylic acid benzyl ester as an impurity, and oxalic acid, to precipitate a solid in methanol or in a mixed solvent containing methanol. It is possible in the production process of the present invention to use a compound which is obtained by reacting (S)-5-(benzyloxyimino)-piperidine-2-carboxylic acid benzyl ester represented by the following formula (4):

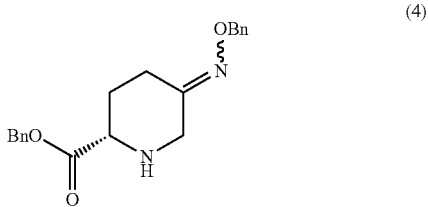 [SMILES: O=C(OCc1ccccc1)[C@@H]1CCC(=NOCc2ccccc2)CN1]

with a reducing agent in the presence of a sulfonic acid, as the compound represented by the above formula (5).

Effect of the Invention

According to the method of the present invention, a cyclic amine compound, which is useful as an intermediate for pharmaceuticals, having an amino group and a carboxyl group as substituents wherein their configuration is trans can be produced with high convenience and high efficiency.

MODE FOR CARRYING OUT THE INVENTION

First, the starting material of the present invention is explained.

The imine derivative used in the present invention is represented by the following formula (1):

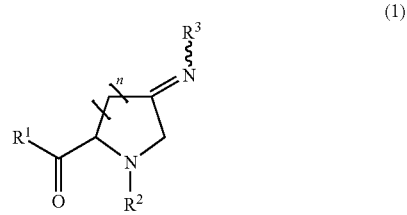

wherein $R^1$ is an organic group forming an ester bond, an amide bond, or a thioester bond with the carbonyl group binding to $R^1$ itself. When $R^1$ forms the ester bond, $R^1$ includes $C_{1-12}$ alkyloxy group, $C_{2-12}$ alkenyloxy group, $C_{7-21}$ aralkyloxy group, $C_{6-18}$ aryloxy group, and silyloxy group wherein $C_{3-36}$ hydrocarbon group binds to silicon atom (such as trialkylsilyloxy group, triarylsilyloxy group, alkylarylsilyloxy group, and others). When $R^1$ forms the amid bond, $R^1$ includes mono-substituted amino group such as amino group, $C_{1-12}$ alkylamino group (mono-alkylamino group), $C_{2-12}$ alkenylamino group (mono-alkenylamino group), $C_{7-21}$ aralkylamino group (mono-aralkylamino group), $C_{6-18}$ arylamino group (mono-arylamino group), and disubstituted amino group, including disubstituted amino group substituted with the same kind of substituents such as $C_{2-24}$ dialkylamino group, $C_{4-24}$ dialkenylamino group, $C_{14-42}$ diaralkylamino group, $C_{12-36}$ diarylamino group and others, and disubstituted amino group substituted with different kinds of substituents such as alkylalkenylamino group and others. When $R^1$ forms a thioester group, $R^1$ includes, for example, thiol group, $C_{1-12}$ alkylthio group, $C_{2-12}$ alkenylthio group, $C_{7-21}$ aralkylthio group and $C_{6-18}$ arylthio group. $R^1$ can be substituted with one or more substituents. Such substituent includes halogen atom, alkoxy group, alkylamino group, dialkylamino group, alkylthio group, and heterocyclic ring.

The alkyloxy group may include cycloalkyloxy group, and the alkylene unit of the alkyloxy group can be substituted with —NH—, —O—, —S—, —S(=O)—, —S(=O)$_2$— or others, and the —NH— can be protected with a protecting group. The examples of such alkyloxy group are specifically methoxy group, ethoxy group, 1-propyloxy group, isopropyloxy group, cyclopropyloxy group, 1-butyloxy group, isobutyloxy group, sec-butyloxy group, tert-butyloxy group, cyclobutyloxy group, 1-pentyloxy group, 2-pentyloxy group, 3-pentyloxy group, isopentyloxy group, neopentyloxy group, cyclopentyloxy group, 1-hexyloxy group, 2-hexyloxy group, 3-hexyloxy group, cyclohexyloxy group, and others.

The alkenyloxy group may include cycloalkenyloxy group, and the alkylene unit of the alkenyloxy group can be substituted with —NH—, —O—, —S—, —S(=O)—, —S(=O)$_2$— or others, and the —NH— can be protected with a protecting group.) The examples of such alkenyloxy group are alkenyloxy group in which the oxygen atom binds to the sp$^3$ carbon atom of the alkenyl group, such as allyloxy group, 2-methyl-1-propen-3-yloxy group, 2-buten-1-yloxy group, 1-methyl-2-buten-1-yloxy group, 2-methyl-2-buten-1-yloxy group, 3-methyl-2-buten-1-yloxy group, 2-penten-1-yloxy group, 1-methyl-2-penten-1-yloxy group, 2-methyl-2-penten-1-yloxy group, 3-methyl-2-penten-1-yloxy group, 4-methyl-2-penten-1-yloxy group, cyclopenten-3-yloxy group, 2-hexen-1-yloxy group, cyclohexen-3-yloxy group, and others; alkenyloxy group in which the oxygen atom binds to the sp$^2$ carbon atom of the alkenyl group, such as vinyloxy group (ethenyloxy group), 1-propen-1-yloxy group, 1-buten-1-yloxy group, 2-buten-2-yloxy group, 1-penten-1-yloxy group, 2-penten-2-yloxy group, 2-penten-3-yloxy group, cyclopenten-1-yloxy group, 1-hexen-1-yloxy group, 2-hexen-2-yloxy group, 2-hexen-3-yloxy group, 3-hexen-3-yloxy group, cyclohexen-1-yloxy group, and others; and others.

The example of the aralkyloxy group includes benzyloxy group, diphenylmethyloxy group, trityloxy group, 1-naphthylmethyloxy group, 2-naphthylmethyloxy group, 1-antracenylmethyloxy group, 2-antracenylmethyloxy group, and 5-antracenylmethyloxy group; the example of the aryloxy group includes phenyloxy group, 1-naphthyloxy group, 2-naphthyloxy group, 1-antracenyloxy group, 2-antracenyloxy group, and 5-antracenyloxy group; and the example of the silyloxy group wherein hydrocarbon group binds to silicon atom includes trimethylsilyloxy group, triethylsilyloxy group, triisopropylsilyloxy group, triphenylsilyloxy group, and tert-butyldiphenylsilyloxy group.

The mono-alkylamino group may include mono-cycloalkylamino group, and the alkylene unit of the mono-alkylamino group can be substituted with —NH—, —O—, —S—, —S(=O)—, —S(=O)$_2$— or others, and the —NH— can be protected with a protecting group. The example of such mono-alkylamino group includes methylamino group, ethylamino group, 1-propylamino group, isopropylamino group, cyclopropylamino group, 1-butylamino group, isobutylamino group, sec-butylamino group, tert-butylamino group, cyclobutylamino group, 1-pentylamino group, 2-pentylamino group, 3-pentylamino group, isopentylamino group, neopentylamino group, cyclopentylamino group, 1-hexylamino group, 2-hexylamino group, 3-hexylamino group, cyclohexylamino group, piperidin-4-ylamino group and the N-protected compounds thereof (for example, N-(benzyloxycarbonyl)-piperidin-4-ylamino group, N-(tert-butoxycarbonyl)-piperidin-4-ylamino group, and others), and others.

The mono-alkenylamino group may include mono-cycloalkenylamino group, and the alkylene unit of the mono-alkenylamino group can be substituted with —NH—, —O—, —S—, —S(=O)—, —S(=O)$_2$— or others, and the —NH— can be protected with a protecting group. The examples of the mono-alkenylamino group are mono-alkenyl amino group in which the nitrogen atom binds to the sp$^3$ carbon atom of the alkenyl group such as allylamino group, 2-methyl-1-propen-3-ylamino group, 2-buten-1-ylamino group, 1-methyl-2-buten-1-ylamino group, 2-methyl-2-buten-1-ylamino group, 3-methyl-2-buten-1-ylamino group, 2-penten-1-ylamino group, 1-methyl-2-penten-1-ylamino group, 2-methyl-2-penten-1-ylamino group, 3-methyl-2-penten-1-ylamino group, 4-methyl-2-penten-1-ylamino group, cyclopenten-3-ylamino group, 2-hexen-1-ylamino group, cyclohexen-3-ylamino group, and others; mono-alkenylamino group in which the nitrogen atom binds to the sp$^2$ carbon atom of the alkenyl group such as ethenylamino group, 1-propen-1-ylamino group, 1-buten-1-ylamino group, 2-buten-2-ylamino group, 1-penten-1-ylamino group, 2-penten-2-ylamino group, 2-penten-3-ylamino group, cyclopenten-1-ylamino group, 1-hexen-1-ylamino group, 2-hexen-2-ylamino group, 2-hexen-3-ylamino group, 3-hexen-3-ylamino group, cyclohexen-1-ylamino group, and others; and others.

The example of the mono-aralkylamino group includes benzylamino group, diphenylmethylamino group, tritylamino group, 1-naphthylmethylamino group, 2-naphthylmethylamino group, 1-antracenylmethylamino group, 2-antracenylmethylamino group, 5-antracenylmethylamino group; and the example of the mono-arylamino group includes phenylamino group, 1-naphthylamino group, 2-naphthylamino group, 1-antracenylamino group, 2-antracenylamino group, and 5-antracenylamino group.

The disubstituted amino group can be dialkylamino group, dialkenylamino group, diaralkylamino group, diarylamino group, and others. The example of the disubstituted amino group includes a group having two substituents, wherein the example of the substituents includes such a group which is listed as the substituents for the above mono-substituted amino group (such as mono-alkylamino group, mono-alkenylamino group, mono-aralkylamino group, and mono-arylamino group), and two of the substituents may be the same or different.

The alkylthio group may include cycloalkylthio group, and the alkylene unit of the alkylthio group can be substituted with —NH—, —O—, —S—, —S(=O)—, —S(=O)$_2$— or others, and the —NH— can be protected with a protecting group. The example of the alkylthio group includes methylthio group, ethylthio group, 1-propylthio group, isopropylthio group, cyclopropylthio group, 1-butylthio group, isobutylthio group, sec-butylthio group, tert-butylthio group, cyclobutylthio group, 1-pentylthio group, 2-pentylthio group, 3-pentylthio group, isopentylthio group, neopentylthio group, cyclopentylthio group, 1-hexylthio group, 2-hexylthio group, 3-hexylthio group, cyclohexylthio group, and piperidinyl-4-thio group.

The alkenylthio group may include cycloalkenylthio group, and the alkylene unit of the alkenylthio group can be substituted with —NH—, —O—, —S—, —S(=O)—, —S(=O)$_2$— or others, and the —NH— can be protected with a protecting group. The example of the alkenylthio group includes alkenylthio group in which the oxygen atom binds to the sp$^3$ carbon atom of the alkenyl group, such as alkylthio group, 2-methyl-1-propen-3-ylthio group, 2-buten-1-ylthio group, 1-methyl-2-buten-1-ylthio group, 2-methyl-2-buten-1-ylthio group, 3-methyl-2-buten-1-ylthio group, 2-penten-1-ylthio group, 1-methyl-2-penten-1-ylthio group, 2-methyl-2-penten-1-ylthio group, 3-methyl-2-penten-1-ylthio group, 4-methyl-2-penten-1-ylthio group, cyclopenten-3-ylthio group, 2-hexen-1-ylthio group, cyclohexen-3-ylthio group, and others; alkenylthio group in which the oxygen atom binds to the sp$^2$ carbon of the alkenyl group, such as ethenylthio group, 1-propen-1-ylthio group, 1-buten-1-ylthio group, 2-buten-2-ylthio group, 1-penten-1-ylthio group, 2-penten-2-ylthio group, 2-penten-3-ylthio group, cyclopenten-1-ylthio group, 1-hexen-1-ylthio group, 2-hexen-2-ylthio group, 2-hexen-3-ylthio group, 3-hexen-3-ylthio group, cyclohexen-1-ylthio group, and others; and others.

The example of the aralkylthio group includes benzylthio group, diphenylmethylthio group, tritylthio group, 1-naphthylmethylthio group, 2-naphthylmethylthio group, 1-antracenylmethylthio group, 2-antracenylmethylthio group, 5-antracenylmethylthio group; and the example of the arylthio group includes phenylthio group, 1-naphthylthio group, 2-naphthylthio group, 1-antracenylthio group, 2-antracenylthio group, and 5-antracenylthio group.

The above R$^1$ is preferably an organic group forming an ester bond (especially aralkyloxy group, alkenyloxy group and others) or an organic group forming an amide bond (especially mono-cycloalkylamino group and others). R$^1$ is more preferably benzyloxy group, allyloxy group, or N-(benzyloxycarbonyl)-piperidin-4-ylamino group. R$^1$ is further more preferably benzyloxy group. The preferable example of R$^1$ includes a group comprising cyclic structure among the above listed groups, for example, cycloalkyloxy group, cycloalkenyloxy group, aralkyloxy group, aryloxy group, mono-cycloalkylamino group, mono-cycloalkenylamino group, mono-aralkylamino group, mono-arylamino group, and a group (group A) in which the monosubstituted amino group listed here is bound further by alkyl group, alkenyl group, aralkyl group, or aryl group, wherein the group A includes dicycloalkylamino group, dicycloalkenylamino group, diaralkylamino group and diarylamino group. The preferable example of R$^1$ also includes cycloalkylthio group, cycloalkenylthio group, aralkylthio group, arylthio group, and others. More preferable group among them is the one having aryl group (especially phenyl group) in part. In addition, the alkylene unit included in the preferable groups can be substituted with —NH—, —O—, —S—, —S(=O)—, —S(=O)$_2$— or others, and the —NH— can be protected with a protecting group.

The above R$^2$ represents hydrogen atom, C$_{1-12}$ alkyl group, C$_{2-12}$ alkenyl group, C$_{7-21}$ aralkyl group, or C$_{6-18}$ aryl group. The groups can be substituted with one or more substituents. As the substituents, similar or same kind of substituents listed for R$^1$ can also be provided as examples.

The example of the alkyl group (including cycloalkyl group) of R$^2$ includes specifically methyl group, ethyl group, 1-propyl group, isopropyl group, cyclopropyl group, butyl group, isobutyl group, sec-butyl group, tert-butyl group, cyclobutyl group, pentyl group, 2-pentyl group, 3-pentyl group, isopentyl group, neopentyl group, cyclopentyl group, hexyl group, 2-hexyl group, 3-hexyl group, and cyclohexyl group.

The example of the alkenyl group (including cycloalkenyl group) of $R^2$ includes alkenyl group having an atomic bonding on the sp³ carbon atom at 1-position such as allyl group, 2-methyl-2-propenyl group, 2-butenyl group, 1-methyl-2-butenyl group, 2-methyl-2-butenyl group, 3-methyl-2-butenyl group, 2-pentenyl group, 1-methyl-2-pentenyl group, 2-methyl-2-pentenyl group, 3-methyl-2-pentenyl group, 4-methyl-2-pentenyl group, 2-cyclopentenyl group, 2-hexenyl group, 2-cyclohexenyl group, and others; and alkenyl group having an atomic bonding on the sp² carbon atom at 1-position such as ethenyl group, 1-propenyl group, 1-butenyl group, 1-ethyl-1-ethenyl group, 1-pentenyl group, 1-propyl-1-ethenyl group, 1-ethyl-1-propenyl group, 1-cyclopentenyl group, 1-hexenyl group, 1-butyl-1-ethenyl group, 1-propyl-1-propenyl group, 1-ethyl-1-butenyl group, 1-cyclohexenyl group, and others.

The example of the aralkyl group of $R^2$ includes benzyl group, diphenylmethyl group, trityl group, 1-naphthylmethyl group, 2-naphthylmethyl group, 1-antracenylmethyl group, 2-antracenylmethyl group, 5-antracenylmethyl group; and the example of the aryl group of $R^2$ includes phenyl group, 1-naphthyl group, 2-naphthyl group, 1-antracenyl group, 2-antracenyl group, and 5-antracenyl group, and others.

$R^2$ is preferably hydrogen atom.

The above $R^3$ represents hydrogen atom, $C_{1-12}$ alkyl group, $C_{2-12}$ alkenyl group, $C_{7-21}$ aralkyl group, $C_{6-18}$ aryl group, hydroxy group, $C_{1-12}$ alkyloxy group, $C_{2-12}$ alkenyloxy group, $C_{7-21}$ aralkyloxy group, or $C_{6-18}$ aryloxy group. The groups can be substituted with one or more substituents. As the substituents, similar or same kind of substituents listed for $R^1$ can also be provided as examples.

The specific examples of the alkyl group (including cycloalkyl group), the alkenyl group (including cycloalkenyl group), the aralkyl group, and the aryl group of $R^3$ are similar as or same as those listed for $R^2$. The alkyloxy group of $R^3$ may include cycloalkyloxy group, and the alkylene unit of the alkyloxy group can be substituted with —NH—, —O—, —S—, —S(=O)—, —S(=O)$_2$—, or the others, and the —NH— can be protected with a protecting group. The alkenyloxy group of $R^3$ may include cycloalkenyloxy group, and the alkylene unit of the alkenyloxy group can be substituted with —NH—, —O—, —S—, —S(=O)—, —S(=O)$_2$—, or the other, and the —NH— can be protected with a protecting group. The specific examples of the alkyloxy group, the alkenyloxy group, the aralkyloxy group, and the aryloxy group of $R^3$ are similar as or same as those listed for $R^1$.

The above $R^3$ is preferably alkyloxy group, alkenyloxy group, aralkyloxy group or aryloxy group, more preferably aralkyloxy group, and especially preferably benzyloxy group.

The above n represents an integer number of 1, 2 or 3, and n is preferably 2.

The steric configuration of $R^3$ can be either E or Z, and the E isomer and the Z isomer can be mixed in an arbitrary ratio.

The above imine derivative (1) is preferably a compound (40) wherein $R^1$ is benzyloxy group, $R^2$ is hydrogen atom, $R^3$ is benzyloxy group, and n is 2, and more preferably (S)-5-(benzyloxyimino)-piperidine-2-carboxilic acid benzyl ester represented by the following formula (4):

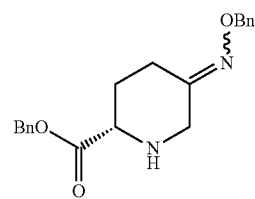

(4)

wherein $R^1$ is benzyloxy group, $R^2$ is hydrogen atom, $R^3$ is benzyloxy group, n is 2, and the carbon atom to which the group $R^1CO$ is connected is in the S configuration. Other preferable example of the above imine derivative (1) is a compound (60) in which $R^1$ is a group represented by the following formula (8):

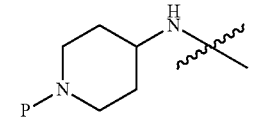

(8)

wherein P represents a protecting group for the amino group; $R^2$ is hydrogen atom; $R^3$ is benzyloxy group; n is 2; and more preferable example is a (S)-5-(benzyloxyimino)-piperidine-2-carboxylic acid derivative represented by the following formula (6):

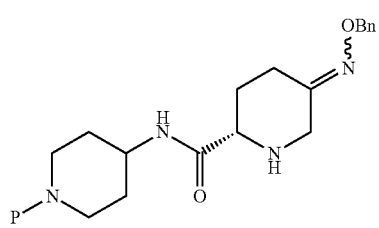

(6)

wherein $R^1$ is a group represented by the above formula (8), $R^2$ is hydrogen atom, $R^3$ is benzyloxy group, n is 2, and the carbon atom to which the group $R^1CO$ is connected is in the S configuration.

The protecting group in the present invention is not particularly restricted as long as the protecting group can protect amino group, and the example of the protecting group includes the protecting group listed in pp. 494-653 of Protective Groups in Organic Chemistry by Theodora W. Greene, Peter G. M. Wuts (the 3rd edition, JOHN WILEY & SONS, INC). The protecting group is preferably a carbamate type protecting group such as methoxycarbonyl group, ethoxycarbonyl group, isopropoxycarbonyl group, tert-butoxycarbonyl group, allyloxycarbonyl group, benzyloxycarbonyl group, phenoxycarbonyl group, and others; an acyl type protecting group such as folmyl group, acetyl group, trichloroacetyl group, trifluoroacetyl group, benzoyl group, p-nitrobenzoyl group, and others; or benzyl group, more preferably an carbamate type protecting group such as methoxycarbonyl group, ethoxycarbonyl group, isopropoxycarbonyl group, tert-butoxycarbonyl group, allyloxycarbonyl group, benzyloxycarbonyl group and phenoxycarbonyl group and others, and especially preferably a carbamate type protecting group such as benzyloxycarbonyl group.

The production process for the above imine derivative can follow the process described in the Patent Document 1, for example. The entire contents of the Patent Document 1 (WO2009/090320) are incorporated by reference herein.

Next, the amine derivative as the resultant compound is explained.

The cyclic amine compound obtained by the present invention is represented either by the following formula (2):

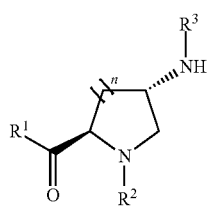

(2)

or by the following formula (3):

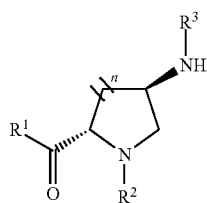

(3)

wherein $R^1$, $R^2$ and $R^3$ are the same as the above. Depending on the combination of the adopted substituent and the reducing agent, $R^1$, $R^2$ or $R^3$ may be reduced, and the present invention also includes such compound (reduced compound). For example, in case either $R^1$, $R^2$ or $R^3$ has alkenyl group and the reducing agent adopted to be used is borane, the alkenyl group may be hydroborated. In case the reducing agent adopted to be used is borohydride compound, the alkenyl group may be reduced.

The amino group obtained by the reduction of the imino group in a compound (1) and the carbonyl group on the ring become in the trans configuration.

The above cyclic amine compound is preferably a compound (50) wherein $R^1$ is benzyloxy group, $R^2$ is hydrogen atom, $R^3$ is benzyloxy group, and n is 2; more preferably (2S,5R)-5-(benzyloxyamino)-piperidine-2-carboxylic acid benzyl ester represented by the following formula (5):

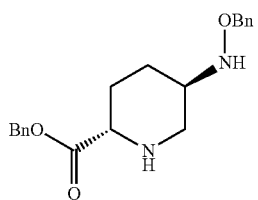

(5)

wherein $R^1$ is benzyloxy group, $R^2$ is hydrogen atom, $R^3$ is benzyloxy group, n is 2, and the carbon atom to which the group $R^1CO$ is connected is in the S configuration. Other preferable example of the above cyclic amine compound is a compound (90) wherein $R^1$ is dibenzylamino group, $R^2$ is hydrogen atom, $R^3$ is benzyloxy group and n is 2, more preferable example is (2S,5R)-5-(benzyloxyamino)-piperidine-2-carboxylic acid dibenzylamide represented by the following formula (9):

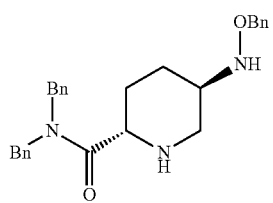

(9)

wherein $R^1$ is dibenzylamino group, $R^2$ is hydrogen atom, $R^3$ is benzyloxy group, n is 2, and the carbon atom to which the group $R^1CO$ is connected is in the S configuration. Other preferable example of the above cyclic amine compound is a compound (70) in which $R^1$ is a group represented by the following formula (8):

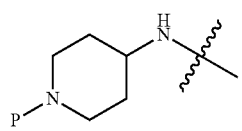

(8)

wherein P represents a protecting group for the amino group; $R^2$ is hydrogen atom; $R^3$ is benzyloxy group; and n is 2; and more preferable example is a (2S,5R)-5-(benzyloxyamino)-piperidine-2-carbocylic acid derivative represented by the following formula (7):

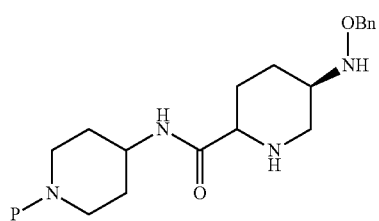

(7)

wherein $R^1$ is a group represented by the above formula (8), and P is the same as the above; $R^2$ is hydrogen atom; $R^3$ is benzyloxy group; n is 2; and the carbon atom to which the group $R^1CO$ is connected is in the S configuration. These preferable cyclic amine compounds are obtained from the corresponding imine derivative of the above: for example, the cyclic amine compound represented by the formula (5) is obtained from the imine derivative represented by the formula (4), and the cyclic amine compound represented by the formula (7) is obtained from the imine derivative represented by the formula (6).

The above amine derivative is obtained by reacting an imine derivative (1) with a reducing agent in the presence of a sulfonic acid. In this reaction, a solvent (a reaction solvent) can be used optionally. By performing the reaction in the presence of a sulfonic acid, it becomes possible to reduce an imine derivative (1) diastereo-selectively. Hereinafter the sulfonic acid used in the present reaction is explained in more details.

The example of the sulfonic acid used in the reaction includes specifically sulfuric acid, alkanesulfonic acid (such as methanesulfonic acid, trifluoromethanesulfonic acid, ethanesulfonic acid, n-propanesulfonic acid, n-butanesulfonic acid, n-pentanesulfonic acid, n-hexanesulfonic acid, isopropanesulfonic acid, and others), cycloalkanesulfonic acid (such as cyclobutanesulfonic acid, cyclopentanesulfonic acid, cyclopropanesulfonic acid, and others), a sulfonic acid in which the $SO_2$ group is connected to the tertiary carbon (such as tert-butanesulfonic acid, adamantylsulfonic acid, camphorsulfonic acid, and others) and arylsulfonic acid (such as benzenesulfonic acid, p-toluenesulfonic acid, p-fluorobenzenesulfonic acid, 2,4,6-trimethylbenzenesulfonic acid, and others). In case the listed sulfonic acid contains an asymmetric carbon, the sulfonic acid can be either an enantiomer or a racemate. The sulfonic acid is preferably sulfuric acid, alkanesulfonic acid (especially methanesulfonic acid), arylsulfonic acid (especially p-toluenesulfonic acid), or a sulfonic acid in which the $SO_2$ group is connected to the tertiary carbon atom (especially camphorsulfonic acid and 2,4,6-trimethylbenzenesulfonic acid), more preferably sulfuric acid, arylsulfonic acid (especially p-toluenesulfonic acid), or a sulfonic acid in which the $SO_2$ group is connected to the tertiary carbon atom (especially camphorsulfonic acid), and especially preferably sulfuric acid or camphorsulfonic acid. In terms of diastereo-selectivity of the reduction reaction, camphorsulfonic acid is especially preferred. The camphorsulfonic acid can be (+)-camphorsulfonic acid, (−)-camphorsulfonic acid, or (±)-camphorsulfonic acid.

The usage amount of the above sulfonic acid relative to 1 mole of an imine derivative (1) is preferably not less than 1 mole and not more than 50 mole, and more preferably not less than 2 mole and not more than 10 mole. The usage amount of the sulfonic acid can be the amount at which the amount of the acidic proton of the sulfonic acid relative to 1 mole of the imine derivative (1) is not less than 1 mole and not more than 50 mole, preferably not less than 2 mole and not more than 10 mole.

The above sulfonic acid can be used directly (for example, directly in the solid state or directly in the liquid state), and specifically can be added directly to the reaction vessel. The sulfonic acid can be used in the form of a solution of the sulfonic acid, and in this case, the sulfonic acid solution can be a solution of the reaction solvent, or as a solution of a solvent which is different from the reaction solvent. The solvent to dilute the sulfonic acid includes the similar or the same solvent listed as the reaction solvent described later. The reaction solvent and the dilution solvent can be the same or different.

The example of the reducing agent used for the reaction includes aluminum hydride (such as lithium aluminum hydride, diisobutyl aluminum hydride, bis(2-methoxyethoxy)aluminum sodium hydride, and others), borohydride (for example, alkali metal borohydride such as lithium borohydride, sodium borohydride, potassium borohydride, and others; calcium borohydride, sodium cyanoborohydride, sodium triacetoxyborohydride, lithium triethylborohydride, lithium tri(sec-butyl)borohydride, potassium tri(sec-butyl) borohydride, and others), tributyltin hydride and borane. In terms of the chemical selectivity, the reducing agent is preferably borohydride (especially alkali metal borohydride) and borane, and especially preferably borane.

The way to use the borane is not particularly restricted, and the borane can be used either in the state of gas, complex, or solution. The borane includes specifically diborane, and borane complex (for example, borane-ether complex such as borane-tetrahydrofuran complex; borane-dimethylsulfide complex; borane-pyridine complex; borane-picoline complex; borane-triethylamine complex, and others) for example. As borane, borane prepared in site can also be used wherein the borane prepared in site is produced by mixing the above borohydride (especially alkali metal borohydride) with one or more compound selected from an acid such as hydrochloric acid, hydrobromic acid, sulfuric acid and others; iodine; and a Lewis acid such as trifluoroborane, aluminum chloride, titanium (IV) tetrachloride and others. The borane prepared in site can be added to the reaction system (into the reaction vessel) after produced outside of the reaction system (in other vessel), or can be produced in the reaction system (in the reaction vessel). The preferable borane is borane complex, and especially borane-ether complex such as borane-tetrahydrofuran complex, and others.

The usage amount of the reducing agent (especially borane) relative to 1 mole of an imine derivative (1) can be not less than 1 mole and not more than 50 mole, and more preferably not less than 2 mole and not more than 10 mole.

The reaction solvent for the reaction of the present invention is not particularly restricted, and hydrocarbon solvent, ether solvent, ester solvent, halogen solvent, nitrile solvent, and other solvent can be used. Specifically, the example of the reaction solvent includes pentane, hexane, heptane, cyclopentane, cyclohexane, cycloheptane, benzene, toluene, xylene, mesitylene, diethyl ether, diisopropyl ether, cyclopentyl methyl ether, tert-butyl methyl ether, tetrahydrofuran, 1,4-dioxane, ethylene glycol dimethyl ether, methyl acetate, ethyl acetate, isopropyl acetate, butyl acetate, methylene dichloride, 1,2-dichloroethane, 1,1-dichloroethane, tetrachloroethane, acetonitrile, benzonitrile for example. The reaction solvent is preferably benzene, toluene, xylene, mesitylene, diethyl ether, diisopropyl ether, cyclopentyl methyl ether, tert-butyl methyl ether, tetrahydrofuran, 1,4-dioxane, ethylene glycol dimethyl ether and acetonitrile, more preferably toluene, cyclopentyl methyl ether, tert-butyl methyl ether, tetrahydrofuran, 1,4-dioxane and acetonitrile, and further more preferably toluene, cyclopentyl methyl ether, tert-butyl methyl ether, tetrahydrofuran and 1,4-dioxane. The solvent may be used by itself, or plural solvents may be mixed to be used.

Since the excess amount of solvent is not preferable from the viewpoints of cost and post-treatment, the usage amount of the reaction solvent relative to 1 part by weight of an imine derivative (1) is preferably not more than 50 parts by weight, and more preferably not more than 20 parts by weight.

The reaction temperature for the present reaction is not particularly restricted, and can be suitably set as long as the reaction temperature is not lower than the freezing point of the reaction solvent, and is not higher than the boiling point of the reaction solvent. As for the lower limit, the reaction temperature is preferably not lower than −78° C., more preferably not lower than −50° C., and especially preferably not lower than −30° C. As for the upper limit, the reaction temperature is preferably not higher than 100° C., more preferably not higher than 50° C., and especially preferably not higher than 20° C.

The adding order is not particularly restricted as long as more amount of a sulfonic acid exits compared with the addition amount of a reducing agent (especially borane) in the reaction system. For example, a reducing agent (especially borane) can be added to a solution containing an imine derivative (1) and a sulfonic acid; a sulfonic acid and a reducing agent (especially borane) can be added alternately to a solution containing an imine derivative (1); and an imine derivative (1), sulfonic acid and a reducing agent (especially borane) can be added alternately to a solvent. In terms of the diastereo-selectivity of the reduction reaction, it is preferable to add a reducing agent (especially borane) to a solution containing an imine derivative (1) and a sulfonic acid, or to add an imine derivative (1) and a reducing agent (especially borane) to a solution containing a sulfonic acid.

As the post-treatment after the reaction, a general process can be performed to obtain or isolate a product from a reaction solution. Specifically, for example, an extraction process can be performed by adding water and an organic solvent such as toluene, ethyl acetate, isopropyl acetate, methyl tert-butyl ether, hexane and others to the reaction solution. A desired substance can be isolated by distilling organic solvents away from the extracted solution, especially by heating the extracted solution under reduced pressure.

Thus obtained desired substance possesses enough degree of purity for the following processes, however, the desired substance can be further purified by a general purification method such as a crystallization, a fractional distillation and a column chromatography, in order to further improve purity.

In the following, the purification method is explained specifically, taking for example the case of producing a specific cyclic amine compound (called a compound (50) hereinafter) in which $R^1$ is benzyloxy group, $R^2$ is hydrogen atom, $R^3$ is benzyloxy group, and n is 2, among the cyclic amine compound (2) or (3). The purification method is also explained taking for more preferable example the case of producing (2S,5R)-5-(benzyloxyamino)-piperidine-2-carboxylic acid benzyl ester (a compound (5)).

At the occasion of producing a compound (50), a cis isomer ((2S,5S) derivative and (2R,5R) derivative) of 5-(benzyloxyamino)-piperidine-2-carboxylic acid benzyl ester may be contained as an impurity, and at the occasion of producing a compound (5), (2S,5S)-5-(benzyloxyamino)-piperidine-2-carboxylic acid benzyl ester may be contained as an impurity (these impurities are called "cis type impurities" hereinafter). In order to eliminate the cis type impurities, for example, it is effective to use the above compound (50) or (5) and oxalic acid with the mole ratio, "the former:the latter", of from 1.2:1 to 1:1.2 for example, preferably from 1.1:1 to 1:1.1 and more preferably from 1.05:1 to 1:1.05, and to form a salt in a mole ratio (the former:the latter) of about 1:1 (theoretically 1:1), in order to precipitate a solid in an appropriate solvent (a single solvent or a mixed solvent). The mixing ratio is not particularly limited when plural solvents are mixed to be used.

As the above solvent (called "purification solvent" hereinafter), water, alcohol solvent, hydrocarbon solvent, ester solvent, ether solvent, ketone solvent, nitrile solvent and other solvents can be used. As the hydrocarbon solvent, the ester solvent and the ether solvent, the solvent listed as the above reduction reaction solvent can also be used. The example of the preferable purification solvent includes water, methanol, ethanol, isopropanol, hexane, heptane, toluene, ethyl acetate, isopropyl acetate, tetrahydrofuran, tert-butyl methyl ether, acetone, 2-butanone and acetonitrile. The preferable solvent includes a single or a mixed solvent of alcohol solvent; specifically methanol, ethanol, isopropanol, a mixed solvent containing methanol, a mixed solvent containing ethanol and a mixed solvent containing isopropanol; more preferably methanol and a mixed solvent containing methanol; and especially preferably methanol. For the mixed solvent containing alcohol solvent, each of the above purification solvent can be mixed to be used, and ester solvent can be mixed to be used preferably.

Since it is not preferable to use too much solvent in terms of cost and after treatment, the amount of the above purification solvent to be used is preferably not more than 50 parts by weight, more preferably not more than 20 parts by weight, further more preferably not more than 10 parts by weight, and especially preferably not more than 5 parts by weight, relative to one part by weight of a salt formed from a compound (50) or (5) and oxalic acid. The lower limit for the usage amount of a purification solvent is not particularly restricted, and the usage amount of a purification solvent is not less than 0.5 parts by weight for example, preferably not less than 1 part by weight, and more preferably not less than 3 parts by weight, relative to 1 part by weight of the above salt.

The process to precipitate a solid is not particularly restricted. For example, the above compound (50) or (5) and oxalic acid may be mixed in a solvent to form a salt, and the salt may be directly precipitated as a solid. Alternatively, a solid may be precipitated by decreasing the solubility of the salt using well-known appropriate method as necessary. Such method is exemplified by the followings:

(a) a method of mixing the above compound (50) or (5) with oxalic acid in a solvent, to precipitate a solid,
(b) a method of mixing the above compound (50) or (5) with oxalic acid in a solvent, and then cooling the mixture to precipitate a solid,
(c) a method of mixing the above compound (50) or (5) with oxalic acid in a solvent, and then concentrating the mixture to precipitate a solid,
(d) a method of mixing the above compound (50) or (5) with oxalic acid in a solvent, and then adding a poor solvent thereto to precipitate a solid,
(e) a method of mixing the above compound (50) or (5) with oxalic acid in a solvent, and then substituting the solvent with a poor solvent for concentration, to precipitate a solid.

The methods (a) to (e) can be appropriately combined to precipitate a solid, and a seed crystal can be added to lead solid precipitation. The above poor solvent includes, for example, a hydrocarbon solvent such as ethyl acetate, toluene, hexane, and others.

In the above methods of precipitating a solid, the operating temperature (the temperature during the solid precipitation) is not particularly restricted, and can be set suitably depending on the kind of the solvent to be used. Preferably, the operating temperature is lower than the temperature at which the salt of the above compound (5) and oxalic acid can be soluble in the adopted single solvent or mixed solvent, and the operating temperature can be set in accordance with the desired amount of the precipitation and the desired quality of the crystal.

The salt of the above compound (5) and oxalic acid precipitated by the above methods can be isolated and collected by a process such as a filtration under reduced pressure, a pressure filtration, or a centrifugal separation, and other processes. In case the diastereomeric excess (ode) decreases because of the remaining mother liquid in the collected solid, the quality can be even more improved optionally by further washing with water or an organic solvent (especially a purification solvent).

The drying method for the crystal is not particularly restricted, and it is preferable to dry under reduced pressure (or dry under vacuum) at about 60° C. or less in order to avoid heat decomposition or melting.

In case the diastereomeric excess (ode) does not increase sufficiently, it is effective to re-precipitate a salt as a solid following the above methods. Specifically it is effective to re-precipitate a solid following the method(s) selected from the above methods (a) to (e). It is also effective to rinse a salt formed from the above compound (50) or (5) and oxalic acid with an appropriate solvent, and it is also effective to re-precipitate a solid by a similar method to the above methods (a) to (e). In the above methods (a) to (e), a salt should be formed from the compound (50) or (5) and oxalic acid, however, the salt formation process is obviously unnecessary in the re-precipitation since the salt exists from the beginning.

The salt of the above compound (50) or (5) and oxalic acid obtained by the above methods may be optionally desalted to obtain the above compound (50) or (5) with the enhanced diastereomeric excess (ode). As the process for desalting, for example, it is effective to separate the compound (50) or (5) from the salt by adding an alkaline aqueous solution of sodium hydroxide, potassium hydroxide, sodium carbonate, potassium carbonate, sodium hydrogen carbonate, potassium hydrogen carbonate or other alkalis to the salt of the above compound (50) or (5) and oxalic acid, next, to extract the separated compound (50) or (5) by using an organic solvent such as ethyl acetate, toluene, methyl tert-butyl ether and others, and to heat the extracted compound (50) or (5) under reduced pressure or to process it in other methods to distil the extraction solvent away.

This application claims priority to Japanese Patent Application No. 2011-079033 filed on Mar. 31, 2011, the entire contents of which are incorporated by reference herein.

EXAMPLES

Hereinafter, the present invention is described in more detail with Examples; however, it is not intended that the present invention is restricted by the Examples in any way.

The yield and the preparation ratio of the each compound used in the present invention were analyzed by high performance liquid chromatography with the following condition.
Column: CAPCELL PAK MG, manufactured by SHISEIDO COMPANY, LTD.
Flow rate: 1.0 ml/min
Detection wave length: 210 nm
Column temperature: 35° C.
Mobile phase A: 0.1% by weight phosphoric acid aqueous solution
Mobile phase B: acetonitrile
Time Program:

| 0 min | A: 70%, B: 30% |
| 30 min | A: 20%, B: 80% |
| 40 min | A: 20%, B: 80% |

The (2S)-5-benzyloxyimino-piperidine-2-carboxilic acid benzyl ester used in the following examples was synthesized in accordance with the Patent Document 1.

Example 1

Production of (2S,5R)-5-benzyloxyamino-piperidine-2-carboxylic acid benzyl ester oxalate Under nitrogen atmosphere, (+)-camphorsulfonic acid (7.93 g, 34.1 mmol) and tetrahydrofuran (15 ml) were added to (2S)-5-benzyloxyimino-piperidine-2-carboxylic acid benzyl ester (2.31 g, 6.84 mmol), and the mixture was cooled down to −16° C. Borane-tetrahydrofuran complex (1.06 M tetrahydrofuran solution, 32.1 ml, 34.0 mmol) was added to the mixture for 1.5 hours, and the obtained mixture was stirred for 18 hours. Saturated sodium hydrogen carbonate aqueous solution (40 ml) was added to the reaction mixture, and the pH of the mixture was adjusted at pH 10.9 with 30% by weight sodium hydroxide aqueous solution. The reaction mixture was extracted with ethyl acetate (40 ml), and the organic layer was washed with water (20 ml) and concentrated under reduced pressure. The residue was analyzed with high performance liquid chromatography to find that the residue contained 1.92 g of the desired substance, and the reduction reaction processed with yield of 83%. The diastereo selectivity was (2S,5R)/(2S,5S)=91.4/8.6 (82.8 ode).

To the above product (0.946 g, 2.78 mmol), ethyl acetate was added to adjust the total weight at 8.63 g. The obtained mixture was heated up to 60° C., and methanol solution (0.875 g) containing oxalic acid (0.228 g, 2.53 mmol) was added for 5 minutes. The obtained reaction mixture was cooled down to room temperature, and the precipitate was filtrated. The precipitate was washed with ethyl acetate (2 ml) for 3 times, and dried under reduced pressure to obtain (2S,5R)-5-benzyloxyamino-piperidine-2-carboxylic acid benzyl ester oxalate (0.903 g, 2.10 mmol, yield: 76%). The diastereo ratio of this solid was (2S,5R)/(2S,5S)=99.3/0.7 (98.6 ode).

To the above solid (0.597 g), methanol (3.0 g) was added, and the obtained mixture was stirred for 1 hour at 60° C. The reaction mixture was cooled down to room temperature, and the precipitate was filtrated. The precipitate was washed with methanol (2 ml) for 2 times, and dried under reduced pressure to obtain (2S,5R)-5-benzyloxyamino-piperidine-2-carboxylic acid benzyl ester oxalate (0.542 g). The diastereo ratio of this solid was (2S,5R)/(2S,5S)=99.93/0.07 (99.9% de).

Example 2

Production of (2S,5R)-5-benzyloxyamino-piperidine-2-carboxylic acid benzyl ester Under nitrogen atmosphere, (±)-camphorsulfonic acid (0.697 g, 3.00 mmol) and tetrahydrofuran (2 ml) was added to (2S)-5-benzyloxyimino-piperidine-2-carboxylic acid benzyl ester (0.169 g, 0.50 mmol), and the mixture was cooled down to −20° C. Borane-tetrahydrofuran complex (1.06 M tetrahydrofuran solution, 2.4 ml, 2.54 mmol) was added to the mixture for 1.5 hours, and the obtained mixture was stirred for 6 hours. The reaction mixture was analyzed with high performance liquid chromatography to find that the reaction mixture contained 0.140 g of the title compound, and the reduction reaction proceeded with yield of 82%. The diastereo selectivity was (2S,5R)/(2S,5S)=87.8/12.2 (75.6% de).

Example 3

Production of (2S,5R)-5-benzyloxyamino-piperidine-2-carboxylic acid benzyl ester Under nitrogen atmosphere, the same process was operated as Example 2 except that 2,4,6-trimethylbenzenesulfonic acid (0.603 g, 3.01 mmol) was used instead of (±)-camphorsulfonic acid. The reaction mixture was analyzed with high performance liquid chromatography to find that the reaction mixture contained 0.098 g of the title compound, and the reduction reaction proceeded with yield of 57%. The diastereo selectivity was (2S,5R)/(2S,5S)=72.2/27.8 (44.9% de).

Example 4

Production of (2S,5R)-5-benzyloxyamino-piperidine-2-carboxylic acid benzyl ester Under nitrogen atmosphere, the same process was operated as Example 2 except that p-toluenesulfonic acid (0.520 g, 3.02 mmol) was used instead of (±)-camphorsulfonic acid. The reaction mixture was analyzed with high performance liquid chromatography to find that the reaction mixture contained 0.115 g of the title compound, and the reduction reaction proceeded with yield of 68%. The diastereo selectivity was (2S,5R)/(2S,5S)=75.6/23.4 (52.2 ode).

Example 5

Production of (2S,5R)-5-benzyloxyamino-piperidine-2-carboxylic acid benzyl ester Under nitrogen atmosphere, the same process was operated as Example 2 except that methanesulfonic acid (0.286 g, 2.98 mmol) was used instead of (±)-camphorsulfonic acid. The reaction mixture was analyzed with high performance liquid chromatography to find that the reaction mixture contained 0.093 g of the title compound, and the reduction reaction proceeded with yield of 52%. The diastereo selectivity was (2S,5R)/(2S,5S)=67.2/32.8 (34.4 ode).

Example 6

Production of (2S,5R)-5-benzyloxyamino-piperidine-2-carboxylic acid benzyl ester Under nitrogen atmosphere, the same process was operated as Example 2 except that sulfuric acid (0.147 g, 1.50 mmol) was used instead of (±)-camphorsulfonic acid. The reaction mixture was analyzed with high performance liquid chromatography to find that the reaction mixture contained 0.133 g of the title compound, and the reduction reaction proceeded with yield of 78%. The diastereo selectivity was (2S,5R)/(2S,5S)=79.5/20.5 (59.0% de).

Example 7

Production of (2S,5R)-5-benzyloxyamino-piperidine-2-carboxylic acid benzyl ester Under nitrogen atmosphere, tetrahydrofuran (3 ml) and sulfuric acid (0.151 g, 1.53 mmol) were added to sodium borohydride (0.101 g, 2.66 mmol). The obtained mixture was added dropwise at −10° C. to the mixture consisting of (2S)-5-benzyloxyimino-piperidine-2-carboxylic acid benzyl ester (0.168 g, 0.50 mmol), (+)-camphorsulfonic acid (0.695 g, 2.99 mmol) and tetrahydrofuran (2 ml) for 0.5 hour. After 22 hours of stirring, the obtained reaction mixture was analyzed with high performance liquid chromatography to find that the reaction mixture contained 0.125 g of the title compound, and the reduction reaction proceeded with yield of 74%. The diastereo selectivity was (2S,5R)/(2S,5S)=81.4/18.6 (62.8% de).

Example 8

Production of 4-[({(2S,5R)-5-[(benzyloxy)amino]piperidin-2-yl}carbonyl)amino]piperidine-1-carboxylic acid benzyl ester (+)-Camphorsulfonic acid (0.350 g, 1.51 mmol) and tetrahydrofuran (1 ml) was added to 4-[({(2S)-5-[(benzyloxy)imino]piperidin-2-yl}carbonyl)amino]piperidine-1-carboxylic acid benzyl ester (0.113 g, 0.25 mmol), and the obtained mixture was cooled down to −20° C. Borane-tetrahydrofuran complex (0.95M, 1.3 ml, 1.24 mmol) was added to the mixture, and after 9 hours of stirring, saturated sodium hydrogen carbonate aqueous solution (5 ml) was added. The reaction mixture was extracted with ethyl acetate (10 ml), and the organic layer was dried with anhydrous sodium sulfate, and then concentrated under reduced pressure to obtain the title compound (95.3 mg) as brown oil (crude yield: 84%). The diastereo selectivity was (2S,5R)/(2S,5S)=93.2/6.8 (86.4% de).

Example 9

Purification of (2S,5R)-5-benzyloxyamino-piperidine-2-carboxylic acid benzyl ester oxalate Methanol (4.78 g) and oxalic acid (0.219 g, 2.43 mmol) was added to 5-benzyloxyamino-piperidine-2-carboxylic acid benzyl ester (0.804 g, 2.36 mmol) having diastereo ratio of (2S,5R)/(2S,5S)=77.4/22.6 (54.8% de), and the obtained mixture was stirred for 2 hours. The precipitate was filtrated, washed with methanol (0.80 g) for 2 times, and dried at 50° C. under reduced pressure to obtain 5-benzyloxyamino-piperidine-2-carboxylic acid benzyl ester oxalate (0.556 g, 1.29 mmol, yield: 55%). The diastereo ratio of this solid was (2S,5R)/(2S,5S)=99.1/0.9 (98.2 ode).

Example 10

Purification of (2S,5R)-5-benzyloxyamino-piperidine-2-carboxylic acid benzyl ester oxalate To 5-benzyloxyamino-piperidine-2-carboxylic acid benzyl ester (0.806 g, 2.37 mmol) having diastereo ratio of (2S,5R)/(2S,5S)=77.4/22.6 (54.8% de), ethanol (4.75 g) and oxalic acid (0.217 g, 2.41 mmol) were added, and the obtained mixture was stirred for 2 hours. The precipitate was filtrated, washed with ethanol (0.80 g) for 2 times, and dried at 50° C. under reduced pressure to obtain 5-benzyloxyamino-piperidine-2-carboxylic acid benzyl ester oxalate (0.947 g, 2.20 mmol, yield: 93%). The diastereo ratio of this solid was (2S,5R)/(2S,5S)=87.2/12.8 (74.5% de).

Example 11

Purification of (2S,5R)-5-benzyloxyamino-piperidine-2-carboxylic acid benzyl ester oxalate To 5-benzyloxyamino-piperidine-2-carboxylic acid benzyl ester (0.857 g, 2.51 mmol) having diastereo ratio of (2S,5R)/(2S,5S)=77.4/22.6 (54.8% de), isopropanol (4.86 g) and oxalic acid (0.227 g, 2.52 mmol) were added, and the obtained mixture was stirred for 2 hours. The precipitate was filtrated, and washed with isopropanol (0.83 g) for 2 times, and dried at 50° C. under reduced pressure to obtain 5-benzyloxyamino-piperidine-2-carboxylic acid benzyl ester oxalate (0.937 g, 2.18 mmol, yield: 87%). The diastereo ratio of this solid was (2S,5R)/(2S,5S)=88.4/11.6 (76.7% de).

Example 12

Production of (2S,5R)-5-benzyloxyamino-piperidine-2-carboxylic acid benzyl ester Under nitrogen atmosphere, tetrahydrofuran (2 ml) was added to (2S)-5-benzyloxyimino-piperidine-2-carboxylic acid benzyl ester (0.168 g, 0.50 mmol), and the mixture was cooled down to −10° C. Sulfuric acid (0.302 g, 3.06 mmol) was added to the mixture, and then sodium borohydride (0.0567 g, 1.50 mmol) was added. After 22 hours of stirring, the reaction mixture was analyzed with high performance liquid chromatography to find that the mixture contained 0.136 g of the title compound, and the reduction reaction proceeded with the yield of 80%. The diastereo selectivity was (2S,5R)/(2S,5S)=80.4/19.6 (60.8% de).

Example 13

Production of 4-[({(2S,5R)-5-[(benzyloxy)amino]piperidin-2-yl}carbonyl)amino]piperidine-1-carboxylic acid benzyl ester To 4-[({(2S)-5-[(benzyloxy)imino]piperidin-2-yl}carbonyl)amino]piperidine-1-carboxylic acid benzyl ester (0.4641 g, 1.00 mmol), tetrahydrofuran (3.2 ml) and acetonitrile (0.8 ml) were added, and the obtained mixture was cooled down to −10° C. Sulfuric acid (0.588 g, 6.00 mmol) and subsequently sodium borohydride (0.113 g, 3.00 mmol) were added to the mixture, and after 21 hours of stirring, saturated sodium hydrogen carbonate aqueous solution (5 ml) was added. The reaction mixture was extracted with ethyl acetate (10 ml), and the extracted mixture was analyzed with high performance liquid chromatography to find that the extracted mixture contained 0.366 g of the title compound, and the reduction reaction proceeded with yield of 79%. The diastereo selectivity was (2S,5R)/(2S,5S)=87.3/12.7 (74.6% de).

Example 14

Production of (2S,5R)-5-benzyloxyamino-piperidine-2-carboxylic acid dibenzylamide Under nitrogen atmosphere, tetrahydrofuran (1.6 ml) and acetonitrile (0.4 ml) were added to (2S)-5-benzyloxyimino-piperidine-2-carboxylic acid dibenzylamide (0.214 g, 0.50 mmol), and the obtained mixture was cooled down to −10° C. Sulfuric acid (0.302 g, 3.06 mmol) was added to the mixture, and then sodium borohydride (0.0757 g, 2.00 mmol) was added. After 22 hours of stirring, ethyl acetate (10 ml) and water (5 ml) were added to the mixture, the pH of the mixture was adjusted at 11 with 30% by weight sodium hydroxide aqueous solution, and the obtained mixture was separated. The organic layer was dried with anhydrous sodium sulfate, and concentrated under reduced pressure to obtain 0.176 g of the title compound (yield: 82%). The diastereo selectivity was (2S,5R)/(2S,5S)=87.7/12.3 (75.4% de).

INDUSTRIAL APPLICABILITY

The present invention is applicable to produce a trans-5-aminopiperidine-2-carboxylic acid derivative, which is useful for an intermediate for pharmaceuticals.

The invention claimed is:

1. A process for producing a cyclic amine compound, comprising the step of reacting an imine derivative represented by the following formula (1):

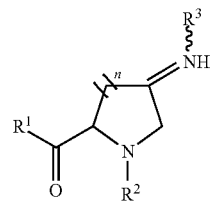

(1)

wherein $R^1$ is $C_{1-12}$ alkyloxy group, $C_{2-12}$ alkenyloxy group, $C_{7-21}$ aralkyloxy group, $C_{6-18}$ aryloxy group, $C_{3-36}$ trialkylsilyloxy group, amino group, $C_{1-12}$ alkylamino group, $C_{2-12}$ alkenylamino group, $C_{7-21}$ aralkylamino group, $C_{6-18}$ arylamino group, $C_{2-24}$ dialkylamino group, $C_{4-24}$ dialkenylamino group, $C_{14-42}$ diaralkylamino group, $C_{12-36}$ diarylamino group, thiol group, $C_{1-12}$ alkylthio group, $C_{2-12}$ alkenylthio group, $C_{7-21}$ aralkylthio group, or $C_{6-18}$ arylthio group; $R^2$ is hydrogen atom, $C_{1-12}$ alkyl group, $C_{2-12}$ alkenyl group, $C_{7-21}$ aralkyl group, or $C_{6-18}$ aryl group; $R^3$ is hydrogen atom, $C_{1-12}$ alkyl group, $C_{2-12}$ alkenyl group, $C_{7-21}$ aralkyl group, $C_{6-18}$ aryl group, hydroxy group, $C_{1-12}$ alkyloxy group, $C_{2-12}$ alkenyloxy group, $C_{7-21}$ aralkyloxy group, or $C_{6-18}$ aryloxy group; and n is an integer of 1, 2, or 3,
with a reducing agent in the presence of a sulfonic acid,
wherein the cyclic amine compound is represented by the following formula (2):

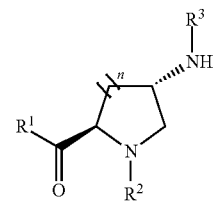

(2)

wherein $R^1$, $R^2$, $R^3$ and n are the same as the above or the following formula (3):

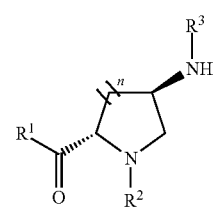

(3)

wherein $R^1$, $R^2$, $R^3$ and n are the same as the above.

2. The process according to claim 1, wherein the sulfonic acid is sulfuric acid or camphorsulfonic acid; and the reducing agent is borane.

3. The process according to claim 1 or 2, wherein $R^1$ is benzyloxy group; $R^2$ is hydrogen atom; $R^3$ is benzyloxy group; and n is 2.

4. The process according to claim 3, further comprising the steps of forming a salt of said cyclic amine compound and oxalic acid, and precipitating the salt as a solid in methanol, in ethanol, in isopropanol, in a mixed solvent containing methanol, in a mixed solvent containing ethanol, or in a mixed solvent containing isopropanol.

5. The process according to claim 1 or 2, wherein $R^1$ is a group represented by the following formula (8):

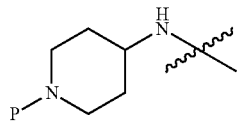

(8)

wherein P represents a protecting group for the amino group;
$R^2$ is hydrogen atom; $R^3$ is benzyloxy group; and n is 2.

6. The process according to claim 5, wherein P is benzyloxycarbonyl group.

7. The process according to claim 1, wherein the sulfonic acid is any one of sulfuric acid, methanesulfonic acid, trifluoromethanesulfonic acid, ethanesulfonic acid, n-propanesulfonic acid, n-butanesulfonic acid, n-pentanesulfonic acid, n-hexanesulfonic acid, isopropanesulfonic acid, cyclobutanesulfonic acid, cyclopentanesulfonic acid, cyclopropanesulfonic acid, tert-butanesulfonic acid, adamantylsulfonic acid, camphorsulfonic acid, benzenesulfonic acid, p-toluenesulfonic acid, p-fluorobenzenesulfonic acid, and 2,4,6-trimethylbenzenesulfonic acid.

8. The process according to claim 1, wherein the reducing agent is any one of lithium aluminum hydride, diisobutyl aluminum hydride, lithium borohydride, sodium borohydride, potassium borohydride, calcium borohydride, sodium cyanoborohydride, sodium triacetoxyborohydride, lithium triethylborohydride, lithium tri(sec-butyl)borohydride, potassium tri(sec-butyl)borohydride, sodium bis(2-methoxyethoxy)aluminum hydride, tributyltin hydride, and borane.

9. The process according to claim 1, wherein the reducing agent is any one of diborane, borane-tetrahydrofuran complex, borane-dimethylsulfide complex, borane-pyridine complex, borane-picoline complex, and borane-triethylamine complex.

10. The process according to claim 1, wherein $R^1$ is dibenzylamino group; $R^2$ is hydrogen atom; $R^3$ is benzyloxy group; and n is 2.

* * * * *